United States Patent [19]

Dorawala et al.

[11] 4,139,496

[45] Feb. 13, 1979

[54] CATALYST FOR DEALKYLATING AN ALKYLAROMATIC HYDROCARBON

[75] Inventors: Tansukhlal G. Dorawala, Wappingers Falls; Russell R. Reinhard, Hopewell Junction; Paul H. Lewis, Poughkeepsie, all of N.Y.

[73] Assignee: Texaco Inc., New York, N.Y.

[21] Appl. No.: 748,447

[22] Filed: Dec. 8, 1976

Related U.S. Application Data

[62] Division of Ser. No. 626,941, Oct. 29, 1975, abandoned.

[51] Int. Cl.$^2$ .................. B01J 21/04; B01J 23/78; B01J 23/86
[52] U.S. Cl. .................. 252/465; 260/672 R
[58] Field of Search .................. 252/470, 465; 260/672 R

[56] References Cited

U.S. PATENT DOCUMENTS

| 2,960,545 | 11/1960 | Seubold | 260/672 R |
| 3,436,434 | 4/1969 | Lester | 260/672 R |
| 3,595,932 | 7/1971 | Maslyansky et al. | 260/672 R |
| 3,649,706 | 3/1972 | Lester | 260/672 R |
| 3,812,196 | 5/1974 | Uchiyama et al. | 260/672 R |

*Primary Examiner*—W. J. Shine
*Attorney, Agent, or Firm*—Thomas H. Whaley; Carl G. Ries; Carl G. Seutter

[57] ABSTRACT

Alkylaromatic hydrocarbons are steam dealkylated in the presence of catalyst, typically containing oxides of nickel, potassium, chromium and aluminum, and particularly characterized by the presence of free nickel metal having a metallic surface area of preferably at least about 8 square meters per gram of catalyst.

3 Claims, No Drawings

CATALYST FOR DEALKYLATING AN ALKYLAROMATIC HYDROCARBON

This is a division of application Ser. No. 626,941, filed Oct. 29, 1975 now abandoned.

FIELD OF THE INVENTION

This invention relates to the conversion of hydrocarbons. More particularly, it relates to the dealkylation of alkylaromatic hydrocarbons such as toluene.

BACKGROUND OF THE INVENTION

As is well known to those skilled in the art, steam demethylation has commonly been carried out by passing an alkylaromatic hydrocarbon, typically toluene, together with steam through a furnace to yield a product containing principally benzene. Steam dealkylation is carried out in the presence of catalysts; and typical catalyst compositions may include zeolites or amorphous inorganic oxides such as silica, alumina, silica-alumina magnesia, zirconia, etc., commonly bearing metal oxides. It is found that typical prior art processes are less than fully satisfactory because of low yields of product, degradation of catalyst, poor product selectivity, etc.

It is an object of this invention to provide a steam dealkylation process particularly characterized by use of a rugged catalyst. Other objects will be apparent to those skilled in the art.

STATEMENT OF THE INVENTION

In accordance with certain of its aspects, the novel process of this invention for dealkylating a monocyclic alkylaromatic hydrocarbon charge may comprise: passing a mixture of steam and a monocyclic alkyl-aromatic hydrocarbon, at steam dealkylating conditions, into contact with an activated catalyst containing Group VIII metal, expressed as metal oxide, in amount of at least about 0.5 weight % when said Group VIII metal is a noble metal or in amount of at least about 6 weight % when said Group VIII metal is iron, cobalt or nickel, and at least a portion of said Group VIII metal being in the form of free metal having a surface area of at least about 8 square meters per gram of total catalyst, thereby forming a product gas containing dealkylated alkylaromatic hydrocarbon; and recovering said product gas.

DESCRIPTION OF THE INVENTION

In accordance with certain of its aspects, the charge alkylaromatic hydrocarbon which may be treated by the process of this invention may be a stream typically having a boiling point of 176° F.–1292° F. (80° C.–700° C.). The stream may contain alkylaromatic hydrocarbons, either pure or in admixture, in varying quantities. This charge stream may typically contain toluene, xylenes, ethyl benzenes, propyl benzenes, etc. The preferred charge hydrocarbon contains a toluene; and in the preferred embodiment it may be substantially entirely toluene se.

Typical charge streams which may be treated by the process of this invention may include aromatic extracts or reformate streams containing alkylaromatic hydrocarbons. Illustrative of such charge streams may be a reformate commonly containing the following components (% by volume):

TABLE

| Component | Broad | Typical |
|---|---|---|
| Paraffins | 30–45 | 40 |
| Olefins | 0–2 | 1 |
| Naphthenes | 1–5 | 3 |
| Aromatics | 45–65 | 56 |

Of the aromatic content of the reformate, 80%–100%, typically 90%, may be present as alkylaromatic hydrocarbons.

This reformate may have a (RON Clear) octane number of 90, an IBP of 115° F., and EBP of 410° F., and an API gravity of 47.7.

Particularly desirable results may be achieved by use, as the hydrocarbon charge, of compositions containing substantial proportions of toluene.

The preferable supported catalyst which may be employed in practice of the process of this invention may comprise an oxide of a Group VIII metal, the catalyst containing at least about 6% by weight of Group VIII metal, expressed as metal oxide. After activation, the catalyst preferably has at least a portion of the Group VIII metal in the form of free metal having a metallic surface area of at least about 8 square meters per gram of total catalyst.

In a preferred embodiment, the supported catalyst may also contain an oxide of a metal of Group I A and of a metal of Group VI B.

The Group VIII metal may include iron Fe, cobalt Co, nickel Ni, ruthenium Ru, rhodium Rh, palladium Pd, osmium Os, iridium Ir, and platinum Pt. Preferably, the Group VIII metal may be nickel or cobalt; and in the most preferred embodiment it is nickel. Although the Group VIII metal may be present in amounts down to 0.5% when it is a noble metal (i.e., Ru, Rh, Pd, Os, Ir or Pt), it is preferred that the minimum be 6% when the Group VIII metal is Fe, Ni or Co. Although it may be possible to have more than one metal of each of the groups present (e.g., Ni and Pt), commonly only one such metal may be present.

The Group VI B metal may be chromium Cr, molybdenum Mo, or tungsten W; and in the preferred embodiment it is chromium Cr.

The Group I A metal, an alkali metal, may be lithium Li, sodium Na, potassium K, rubidium Rb, or caesium Cs. In the preferred embodiment it is potassium K.

The catalyst support may be active or inactive or inert. Typically, the support may be a clay, a silica, a metal oxide, a zeolite, etc. The preferred porous materials may include alumina, silica, silica-alumina, silica-magnesia, silica-titania, silica-beryllia, silica-zirconia, silica-alumina-magnesia, etc. The preferred support is an inert support such as alumina, preferably gamma-alumina.

In typical practice of the process of this invention, the catalyst composition may contain the following components in the indicated parts by weight (expressed as oxide):

TABLE

| Component | Broad | Preferred | Typical |
|---|---|---|---|
| Group VIII | 0.5–40 | 0.5–20 | 15 |
| Fe—CO—Ni | 6–40 | 6–20 | 15 |
| or |  |  |  |
| Ru—Rh—Pd |  |  |  |
| Os—Ir—Pt | 0.5–10 | 0.5–5 | 1 |
| Group VI B | 0–40 | 10–38 | 15 |
| Group I A | 0–5 | 1–4 | 2 |
| Support | 15–99.5 | 38–84 | 68 |

The preferred catalyst may be that containing nickel-chromium-potassium-aluminum; and the catalyst composition may contain the following (expressed as oxide):

TABLE

| Component | Broad | Preferred | Typical |
|---|---|---|---|
| Ni | 6–40 | 6–20 | 15 |
| Cr | 0–40 | 10–38 | 15 |
| K | 0–5 | 1–4 | 2 |
| Al | 15–95 | 38–84 | 68 |

In terms of molar proportions, the catalyst may be represented by the formula:

$$a\ (VIII)_{2/n}O : b\ (VI)_{2/m}O : c\ (I)_2O$$

wherein (VIII) represents a metal of Group VIII of the Periodic Table having a valence n, (VI) represents a metal of Group VI B of the Periodic Table having a valence m, and (I) represents a metal of Group I A of the Periodic Table. a may be 0.002–0.75, preferably 0.002–0.38, say 0.20; b may be 0–0.78, preferably 0.13–0.75, say 0.29; and c may be 0–0.17, preferably 0.003–0.13, say 0.02.

In the preferred embodiment, the catalyst may be represented by the formula:

$$a\ NiO : b\ Cr_3O : c\ K_2O$$

wherein a is 0.08–0.54, preferably 0.08–0.27, say 0.20; b is 0–0.78, preferably 0.21–0.75, say 0.29; and c is 0–0.05, preferably 0.01–0.04, say 0.02.

When the support is alumina, as in the preferred embodiment, the catalyst composition may be represented by the formula:

$$a\ NiO : b\ Cr_3O : c\ K_2O : d\ Al_2O_3$$

wherein a, b and c are as supra and d is 0.15–0.93, preferably 0.38–0.83, say 0.68.

In practice of this invention, the catalyst may be prepared by immersing a catalyst support in a solution containing the metal ions. The support, typically a gamma-alumina extrudate of 1.5 mm diameter and 10 mm length, may first be steam sintered at 900–1400° F., say 1110° F., for 5–25 hours, say 12 hours. During sintering, there may be passed through the bed air at VHSV (STP) of 40–600, say 230, together with steam at water VHSV of 0.05–0.1, say 0.06. The steamed alumina is then calcined for 1–5, say 2, hours at 900° F.–1200° F., say 1000° F. The initial surface of the alumina, typically 200–400, say 231, meter $^2$/gram, may be decreased to 70%–95%, say about 83%, to a value of 140–380, say 192, meter $^2$/gram.

The support (242 parts), preferably as so treated, is cooled to 32° F.–80° F., say about 32° F., and wetted with 200–2525 parts, say 890 parts, of solution prepared by dissolving soluble, decomposable salts of metals of Group VI B and Group I A in aqueous solution. Preferably 0–1000 parts, more preferably 200–1000, say 792 parts, of salt of Group VI B metal, typically chromium nitrate nonahydrate, $Cr(NO_3)_3 \cdot 9H_2O$, and 0–25 parts, preferably 10–23, say 17.2 parts, of salt of Group I A metal, typically potassium nitrate, are dissolved in 10–1500 parts, say 80 parts, of water to yield total solution in amount of 15–2525 parts, say 890 parts. (Although nitrates of the metals are preferably employed, acetates, formates, citrates or other soluble, decomposable salts may be used.)

The solution is poured over the support and is stirred intermittently for 0.5–10 hours, say 1 hour, and the solution (50–2400 parts, typically 731 parts) may then be decanted. The impregnated support is dried at 212° F.–400° F., say 300° F., then heated to decomposition temperature of typically 650° F.–1000° F., say 700° F., and calcined for 1–10 hours, say 2 hours, at 700° F.–1400° F., say 1000° F. This procedure is preferably repeated 2–4, preferably 2, times more until all the metal salt solution is absorbed by the support. The composition so prepared in amount of 242–1500 parts, say 383 parts, may be characterized by the formula:

$$b\ (VI)_{2/m}O \cdot c\ (I)_2O \cdot d\ Al_2O_3$$

wherein (VI) represents a metal having valence m of Group VI B of the Periodic Table, (I) represents a metal of Group I A of the Periodic Table, b is 0–0.78, preferably 0.13–0.75, say 0.74, c is 0–0.1, preferably 0.011–0.13, say 0.02, and d is 0.15–0.93, preferably 0.38–0.83, say 0.59. (Supports other than or in addition to $Al_2O_3$ may be present.)

In the preferred embodiment, the composition may be:

$$b\ Cr_3O : c\ K_2O : d\ Al_2O_3$$

where b = 0.25, c = 0.02, d = 0.59.

292–1500 parts, say 383 parts, may be cooled to 32° F.–80° F., say 32° F., and impregnated with an after-deposited decomposable soluble salt of a Group VIII metal. Preferably the solution may contain 50–700 parts, say 267 parts, of $Ni(NO_3)_2 \cdot 6H_2O$ in 50–1400 parts, say 263 parts, of water. After 0.5–10 hours, say 1 hour, of intermittent stirring, the excess non-absorbed solution is decanted and the solids dried for 2–18 hours, say 16 hours, at 212° F.–400° F., say 300° F. The dried solid is reimpregnated with the remaining salt solution for 0.5–10 hours, say 1 hour, and dried again for 2–18 hours, say 16 hours, at 212° F.–400° F., say 300° F. Further treatment includes heating for 0.5–24 hours, say 1 hour, at 650° F.–1000° F., say 700° F., in a flowing stream of air to decompose the decomposable salts, typically nitrates, and then calcining for 1–10 hours, say 2 hours, at 600° F.–1000° F., say 700° F., to yield 260–1850 parts, say 462 parts, having a density of 0.7–1.5, say 1.11.

The product catalyst so prepared may be characterized by the formula:

$$a\ (VIII)_{2/n}O : b\ (VI)_{2/m}O : c\ (I)_2O : d\ (Sup)$$

wherein all the symbols are as noted supra except that a is 0.002–0.75, preferably 0.002–0.38, say 0.20; (VIII) represents a metal, having a valence n, of Group VIII of the Periodic Table, preferably nickel; and (Sup) represents the catalyst support, preferably $Al_2O_3$.

It will be apparent that when the catalyst composition does not contain an oxide of a Group VI B or of a Group I A metal, certain of the above steps may be omitted; and specifically in that instance, the first and only solution with which the cooled calcined catalyst is contacted is that solution which contains Group VIII metal.

Preferred catalyst compositions may have the formulae:

$$0.23\ NiO : 0.02\ K_2O : 0.73\ Al_2O_3$$

$$0.25\ NiO : 0.27\ Cr_3O : 0.02\ K_2O : 0.64\ Al_2O_3$$

$$0.17\ NiO : 0.65\ Cr_3O : 0.02\ K_2O : 0.51\ Al_2O_3$$

0.20 CoO : 0.20 Cr₃O : 0.02 Na₂O : 0.34 SiO₂

Expressed on a weight basis, the catalyst may have the composition set forth in the following table:

TABLE

| Component | Broad | Preferred | Typical |
|---|---|---|---|
| $(VIII)_{\frac{2}{n}}O$ | 0.5–40 | 0.5–20 | 15 |
| Fe—Co—Ni Ru—Rh—Pd | 6–40 | 6–20 | 15 |
| Os—Ir—Pt | 0.5–10 | 0.5–5 | 1 |
| $(VI)_{\frac{2}{m}}O$ | 0–40 | 10–38 | 15 |
| $(I)_2O$ | 0–5 | 1–4 | 2 |
| (Sup) | 15–99.5 | 38–84 | 68 |

A preferred composition may contain 17.7% NiO, 13.2% $Cr_2O_3$, 1.9% $K_2O$, and 61.6% $Al_2O_3$. Another preferred composition may contain 11.9% NiO, 30.4% $Cr_2O_3$, 1.4% $K_2O$, and 48.2% $Al_2O_3$. Another preferred composition may contain 15.5% NiO, 1.8% $K_2O$, and 74.1% $Al_2O_3$; percentages in this paragraph being on a weight basis.

The catalyst composition of this invention may be prepared by impregnating the support with solutions of metals of Groups VIII, VI B, and I A. Typically, for example, it may be found that the catalyst may be prepared by:

(a) impregnating the support sequentially with several solutions each containing one or more of the metals and thereafter drying and calcining;

(b) impregnating the support with one or more solutions containing less than all of the metals (i.e., species or amount), drying and/or calcining, thereafter impregnating the support with the remaining metals, and drying and/or calcining; etc.

It is unexpectedly found, however, that substantially superior results are achieved (in terms of conversion, yield and/or selectivity) if the Group VI B and I A metals are impregnated, dried and calcined on the catalyst support prior to the impregnation thereof with the Group VIII metal.

In the preferred embodiment, the catalyst support may thus be prepared by impregnating the support, typically alumina, with one solution containing soluble decomposable salts of the Group VI B and Group I A metals, typically chromium and potassium, drying and calcining, thereafter impregnating the so-obtained pre-catalyst with a solution of a soluble decomposable salt of the Group VIII metal, typically nickel, and drying and calcining. Catalyst containing the after-deposited Group VIII metal (i.e., the Group VIII metal deposited after the Group VI B and Group I A metals are present with the support) are particularly characterized by high yields of dealkylated product. Preferably at least a portion of the Group VIII metal (more preferably a major portion, i.e., greater than 50%) is after-deposited.

In the preferred embodiment, the catalyst composition may be in the form of pellets, cylinders or randomly shaped particles; a typical catalyst composition may be in the form of cylinders of diameter 1–15 mm, say 1.5 mm, and height 1–15 mm, say 8–10 mm.

It is a feature of the preferred catalyst of this invention that is be activated prior to use (e.g., in steam dealkylation). Preferably, activation may be carried out by the process which comprises:

(a) maintaining the unactivated catalyst in a hydrogen atmosphere at 750° F.–1400° F. for 10–30 hours, thereby forming a hydrogen-treated catalyst;

(b) maintaining the hydrogen-treated catalyst in a steam-hydrogen atmosphere at 750° F.–1400° F. for 2–10 hours, thereby forming a steamed hydrogen-treated catalyst; and (c) preferably cooling the steamed hydrogen-treated catalyst to 650° F.–900° F. in a steam or steam-hydrogen atmosphere, thereby forming an activated catalyst.

Activation of the steam dealkylation catalyst of this invention may preferably be carried out after the catalyst is in place in the reaction vessel. The vessel may be filled with catalyst composition to a bed bulk density of 50–80 pcf, say 70 pcf. In the first portion of the activation operation, the catalyst composition is heated to 750° F.–1400° F., preferably 900° F. 14 1100° F., say 1100° F., in the presence of a reducing gas containing at least about 30 mole % hydrogen. The gas will preferably be substantially free of active components (other than hydrogen) which are capable of reacting with any of the materials in the system. It is particularly desirable that the gas be free of oxidizing components, including oxygen.

The gas may contain (in addition to hydrogen) helium or, more preferably, light paraffins such as methane, ethane, propane, etc. Hydrogen may be present typically in amount of 30 mole %–100 mole %, preferably 80 mole %–100 mole %, say 100 mole %; i.e., the preferred embodiment may be that in which the gas consists essentially of hydrogen.

Preferably the catalyst composition may be maintained for 10–30 hours, typically 14–16 hours, say 15 hours, in a stream of flowing hydrogen typically flowing at a space velocity VHSV (STP) greater than about 3, more preferably greater than 100, say 100–500, typically 300.

When activation is carried out at atmospheric pressure, as in the preferred embodiment, the partial pressure of hydrogen may be at least about 9 psia (400 mm Hg), preferably 12–15 psia, say 15 psia (760 mm Hg).

In the preferred second portion of the activation cycle, the hydrogen-treated catalyst may be maintained at 750° F.–1400° F., preferably 900° F.–1100° F., say 1100° F. (most preferably at about the same temperature as that employed in the first portion) in a flowing stream of hydrogen and steam. This stream may contain 15–50 mole %, preferably 20–40 mole %, say 30 mole %, of hydrogen; 50–85 mole %, preferably 60–80 mole %, say 70 mole %, of steam; and 0–10 mole %, preferably 0–5 mole %, say about 0 mole %, of inert gas such as helium, nitrogen or light paraffins. Preferably the gas may consist essentially of hydrogen and steam in molar ratio of 0.2–1, typically 0.25–0.67, say 0.42.

When activation is carried out at atmospheric pressure, as in the preferred embodiment, the partial pressure of hydrogen may be 100–380, preferably 150–300, say 240, mm Hg; and the partial pressure of steam may be 380–660, preferably 460–610, say 520, mm Hg.

The second portion of the activation procedure may be carried out for 2–10 hours, preferably 2–5 hours, say 2 hours, in a stream of flowing gas at a space velocity VHSV (STP) greater than about 1.5 preferably greater than 50, say 50–250, typically 150.

Post-activation cooling is typically carried out by maintaining the activated catalyst in a stream of flowing steam for 1–10 hours, preferably 1–5 hours, say 2 hours, as the temperature is lowered to the steam dealkylation temperature of 600° F.–950° F., preferably 650° F.–900° F., say 800° F. Preferably steam is present during post-activation in amount of 50–100 mole %, typically 80–100 mole %, say about 100 mole %, of the flowing stream.

It is a feature of the catalyst of this invention that, in the activated form, it is characterized by the presence of Group VIII metal, preferably nickel, in the form of metal. The catalyst as prepared contains Group VIII metal as oxide; and this oxide must be reduced at least in part prior to use as steam demethylation catalyst. Reduction, during activation, is sufficient to reduce at least a portion of the Group VIII metal oxide to metal. The activated or reduced catalyst may normally contain, e.g., 15–100 mole %, preferably 50–100 mole %, say 70 mole %, of the Group VIII metal in the form of metal and the remainder in a combined form such as the oxide or aluminate.

Thus, the activated or reduced catalyst may be characterized by the formula:

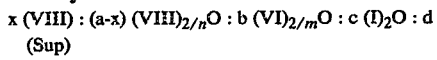
(Sup)

wherein the symbols a, b, c and d are as noted supra and x is 0.0003–0.75, preferably 0.001–0.38, say 0.14. This is equivalent to saying that activation has reduced a portion of the oxide of the Group VIII metal to the free metal; and the free metal is present in mole percent of preferably 50–100%, say 70%, of the total of metal plus oxide.

In the preferred embodiment, the activated catalyst may be:

where x is 0.01–0.54, preferably 0.04–0.27, say 0.14, and the other values are as above. In this instance, this is equivalent to saying that of the total nickel content of metal and oxide 15%–100%, preferably 50%–100%, say 70%, by weight is in the form of nickel metal.

It is a feature of the catalysts of this invention that measurement of the surface area of the free Group VIII metal present reveals that the steam dealkylation process of this invention may be carried out to give yields above about 80% when that surface area is greater than about 8 square meters per gram of total activated catalyst composition. Preferably the surface area may be 8–24, say 8, square meters per gram as determined, e.g., by the nickel metal content (by intensity of the diffraction line) and metallic nickel weight average crystal size.

It may be found that in comparable catalyst systems (which otherwise comply with the requisite criteria herein noted) having a Group VIII metal surface area less than about 8 square meters per gram of total catalyst, when used to demethylate toluene by steam demethylation at 800° F., give conversion in amount less than about 80% in typical runs. Commonly, for example, the curve of conversion, plotted as a function of area, is flat above about 8 square meters per gram and decreases linearly (with a statistical confidence in a non-zero slope of the least squares line being greater than 99.75%) to 0% toluene conversion at 0 square meters per gram.

Steam dealkylation of the hydrocarbon charge may be carried out by passing the charge at 600° F.–950° F., preferably 650° F.–900° F., say 800° F., and pressure of 0–400 psig, preferably 0–200 psig, say 0 psig, together with steam in amount of 2–25 moles, preferably 3–15 moles, say 6 moles, per mole of hydrocarbon charge (corresponding to 100%–1250%, preferably 150%–750%, say 300%, of the stoichiometric quantity) to a reaction zone. In commercial practice it may be desirable to operate at, e.g., 125 psig.

During steam dealkylation at these conditions, alkyl groups are removed from the charge alkylaromatic hydrocarbons to form product hydrocarbons bearing lesser numbers of alkyl groups on the aromatic nuclei. When the charge hydrocarbon contains ethylbenzenes for example, the product stream may contain dealkylated products including benzene. When the charge hydrocarbon contains xylenes, the product stream may contain toluene, benzene, etc. When the charge hydrocarbon stream contains toluene, as in the preferred embodiment, the product hydrocarbon stream may contain benzene. In addition, the product hydrocarbon stream may contain the paraffin derived from the charge, e.g., ethane or methane; and it may contain unreacted charge hydrocarbons in addition to other by-products.

Product hydrocarbon may be withdrawn from the reaction vessel and condensed. The liquid condensate may represent a recovery of 50–94 mole %, preferably 70–94 mole %, say 85 mole %, of the hydrocarbon charged.

In the case of a pure toluene charge, for example, the product (moles per 100 moles of charge toluene) may contain the following:

TABLE

| Component | Broad | Preferred | Typical |
|---|---|---|---|
| Unreacted toluene | 4–79 | 13–70 | 37 |
| Benzene | 20–61 | 30–60 | 55 |
| Hydrogen | 60–183 | 90–180 | 165 |
| $CO_2$ | 20–61 | 30–60 | 55 |

In practice of the process of this invention according to the one embodiment, the reaction is carried out on a short-cycle basis; i.e., the reaction proper (with a charge of steam and hydrocarbon) is carried out for 0.5–3.0 minutes, preferably 0.5–2.0 minutes, say 1 minute, and then the catalyst is regenerated by shutting off the flow of hydrocarbon (and contacting it with the hydrocarbon-free steam) for 1.5–15 minutes, preferably 1–8 minutes, say 3 minutes. The ratio of regeneration time to reaction time may be 1–5, preferably 2–4, say 3.

It is found during practice of the process of this invention that it is possible to achieve improved catalyst activity. For example, the toluene conversion (in terms of mole percent of toluene charge converted) may be 50%–90%, typically 85%–95%, say 90%, in the preferred embodiment in contrast to comparable processes wherein the corresponding values are less than 45%.

It is also a feature of the process of this invention in its preferred embodiment that it permits attainment of benzene yield (in terms of mole percent of the charge toluene converted to benzene) which may be 40%–60%, typically 50%–55%, say 54%. Comparable processes may achieve benzene yields of less than about 35% and commonly 10%–20%.

The novel process permits attainment of these conversions and yields with a high selectivity. The selectivity (in terms of mole percent of benzene recovered in the products per 100 moles of toluene converted) may approach 95% and may commonly be 65%–90%.

It is also a feature of this invention that the catalyst is found to be characterized by increased steam stability and durability. Although it may be found that the crush strength (in pounds) of the alumina support may decrease by as much as 50% during steaming, it is unexpectedly found that the crush strength of the catalyst of this invention (with an alumina support) is essentially equal to the crush strength of fresh alumina support; and this crush strength (and the surface area of the catalyst) may unexpectedly remain essentially constant or increase during steaming.

It is also a feature of the catalyst of this invention that it is possible to achieve these desirably improved novel results by use of a catalyst composition which unexpectedly contains such a low concentration of nickel. Typically, the catalyst composition of this invention contains about 6%–40%, preferably 6%–20%, say 15%, by weight of nickel metal. The preferred prior art catalysts typically contain 15%–80%, preferably 30%–70%, say 63%, nickel metal. The ability to obtain outstanding results by use of a catalyst containing one-third or less nickel permits substantial savings in capital costs in terms of cost of nickel.

It is found, however, that steam demethylation in practice of the process of this invention is achieved if the concentration of Group VIII metal (typically as nickel) is above about 6% by weight (i.e., when expressed as nickel oxide). Nickel content below this yields undesirably low conversion. Although it may be desirable to increase the metal concentration up to about 20% when the Group VIII metal is Fe, Co or Ni, satisfactory results are commonly attainable at 6%–10%. In the case of the noble Group VIII metals (Ru, Rh, Pd, Os, Ir, Pt), the metal content may be as low as 0.5%.

DESCRIPTION OF THE PREFERRED EMBODIMENTS

Practice of the process of this invention will be apparent to those skilled in the art from the following illustrative embodiments wherein, as elsewhere in this description, all parts are parts by weight unless otherwise specifically stated.

EXAMPLE I

In this control example, a catalyst is to be prepared corresponding to the formula:

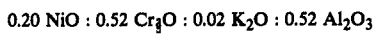
0.20 NiO : 0.52 Cr$_3$O : 0.02 K$_2$O : 0.52 Al$_2$O$_3$

The catalyst support is gamma-alumina in the form of cylinders of average height 10 mm and diameter 1.5 mm (Aero 100 brand product of American Cyanamid) and is possesses a surface area of 231 square meters per gram. The support is steam sintered in a stainless steel tubular reactor by heating to 1110° F. for 12 hours while in contact with a moving stream containing 64 grams per hour of water and 8.0 cubic feet per hour of air. After 12 hours, the steam is shut off and the alumina is calcined at 1000° F. for 2 hours in a stream of air (8.0 cubic feet per hour). The surface area of the calcined alumina is 192 m$^2$/g.

318 parts of this calcined alumina are placed within a container and chilled to 32° F. The chilled alumina is wetted with an aliquot (400 parts) of a solution prepared by dissolving 446 parts of nickelous nitrate hexahydrate, Ni(NO$_3$)$_2$.6H$_2$O, 950 parts of chromium nitrate nonahydrate, Cr(NO$_3$)$_3$.9H$_2$O, and 25.7 parts of potassium nitrate, KNO$_3$, in 150 parts of water — yielding 1100 parts of total solution. The so-wetted support is dried at 300° F. for 2 hours, the nitrates decomposed at 700° F., and the support then calcined for 2 hours at 1000° F. The dry material is subjected to the same sequence again to absorb the entire solution onto the support. The final product, after the second calcining at 700° F. (to decompose the nitrates), is further calcined for 2 hours at 1000° F. to yield 582 parts of control catalyst.

The catalyst actually corresponds to:

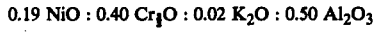
0.19 NiO : 0.40 Cr$_1$O : 0.02 K$_2$O : 0.50 Al$_2$O$_3$

In this control example, the catalyst is then reduced in hydrogen for 4 hours at 750° F., and further reduced in hydrogen for 4 hours at 900° F. The reduced catalyst is pressured to 500 psig with carbon monoxide, warmed to 140° F., and allowed to stand for 2 hours during which time the pressure dropped to 470 psig. The catalyst is then heated to 400° F., rapidly depressurized to about atmospheric pressure, and cooled to 25° C. in flowing nitrogen.

The catalyst is then further reduced in flowing hydrogen at 900° F. for 14–16 hours to yield a product reduced catalyst containing 2.9 weight % metallic nickel.

EXAMPLE II

In this control example, a catalyst is prepared corresponding to the formula:

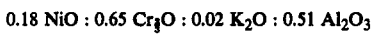
0.18 NiO : 0.65 Cr$_1$O : 0.02 K$_2$O : 0.51 Al$_2$O$_3$ and containing 12.2% NiO, 30.3% Cr$_2$O$_3$, 1.8% K$_2$O, and 47.8% Al$_2$O$_3$.

166 parts of calcined alumina (treated as in Example I) are placed within a container and chilled to 32° F. the chilled alumina is wetted with an aliquot of a solution prepared by dissolving 217 parts of nickelous nitrate hexahydrate, Ni(NO$_3$)$_2$.6H$_2$O, 700 parts of chromium nitrate nonahydrate, Cr(NO$_3$)$_3$.9H$_2$O, and 15 parts of potassium nitrate, KNO$_3$, in 80 parts of water — yielding 1012 parts of total solution. The so-wetted support is dried at 300° F. for 2 hours, the nitrates decomposed at 700° F., and the support then calcined for 2 hours at 1000° F. The dry material is subjected to the same sequence twice more to absorb the entire solution onto the support. The final product, after the last calcining at 700° F. (to decompose the nitrates), is further calcined for 2 hours at 1000° F., and it is then reduced in hydrogen at 900° F. for 14–16 hours to yield a product containing 3.4 weight % nickel metal.

EXAMPLE III

In this control example, a nickel-potassium on silica catalyst is prepared. A potassium hydroxide solution (1.7 parts of KOH in 100 parts of water) is poured onto 145 parts of silica (Girdler brand T-869 silica carrier — one-eighth inch extrudates). The mixture is thoroughly mixed, dried at steam temperature, and calcined at 600° F. for 3 hours.

A solution containing 29.7 parts of nickelous nitrate hexahydrate in 100 parts of water is poured over the calcined extrudates. The mixture is dried at steam temperature, heated in flowing air at 500° F. for 3 hours to decompose the nitrates, and calcined at 1000° F. for 2 hours to give 150 parts of catalyst.

The catalyst is reduced in hydrogen at 1200° F. for 16 hours to yield product containing 5.0% by weight of metallic nickel which assayed to a little more than 100% (sic) of the nickel content.

EXAMPLE IV

In this control example, the calcined alumina support is prepared as in Example I.

In the first portion of this example, 242 parts of calcined alumina are soaked with an aliquot of a solution prepared by dissolving 395 parts of chromium nitrate nonahydrate and 21.5 parts of potassium nitrate in 1000 parts of water. After one hour, the remaining solution is decanted and the impregnated support is dried at 300° F., nitrate-decomposed at 700° F., and calcined for 2 hours at 1000° F. The procedure is repeated twice more until all the metal salt solution is absorbed by the initial charge of alumina.

In this second portion of this example, 131 parts of this pre-catalyst are cooled to 32° F. and impregnated with a solution of 38.2 parts of nickelous nitrate hexahydrate in 300 parts of water. The excess solution is decanted. The catalyst is dried at 300° F. and the cooled catalyst is reimpregnated with the remaining solution and dried again at 300° F. The catalyst is then nitrate-decomposed in air at 700° F. for 2 hours and calcined further in air at 700° F. for 2 hours. The product catalyst composition (211 parts of density 1.11) corresponds to the formula:

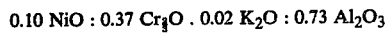
$$0.10\ NiO : 0.37\ Cr_3O . 0.02\ K_2O : 0.73\ Al_2O_3$$

and contains 6.8% NiO, 14.4% $Cr_2O_3$, 2.1% $K_2O$, and 68.8% $Al_2O_3$.

This catalyst is then reduced in hydrogen at 900° F. for 14-16 hours to yield product containing 3.4% by weight of metallic nickel.

EXAMPLE V

In this control example, a commercially-available supported catalyst containing nickel oxide (Girdler brand T-314 catalyst tablets containing 8%-10% nickel as the oxide on activated alumina) is reduced in hydrogen at 1200° F. for 16 hours to yield a product containing 2.7% by weight of metallic nickel.

EXAMPLE VI

In this experimental example carried out in accordance with practice of the process of this invention, the catalyst having the formula:

$$0.19\ NiO : 0.49\ Cr_3O : 0.02\ K_2O : 0.50\ Al_2O_3$$

is prepared (but not subjected to reduction and further treatment) as in Example I, is reduced in hydrogen for 4 hours at 750° F., then for 6 hours at 1200° F., and then for 14-16 hours at 900° F. The product so obtained contains 10.0% by weight of metallic nickel.

EXAMPLE VII

In this experimental example which represents practice of the process of this invention, the support used is American Cyanamid Aero 100 brand, one-sixteenth inch extrudates of gamma-alumina.

Prior to use, the alumina is charged into a stainless steel tubular reactor and heated to 1110° F. for 12 hours while passing 64 grams/hour of water and 8.0 cubic feet/hour of air through the bed. The steamed alumina is then calcined for 2 hours at 1000° F. The surface area of the alumina is reduced by this treatment from an initial value of 231 $m^2/g$ to a final value of 192 $m^2/g$.

166 parts of steam sintered alumina support are placed within a container and chilled in an ice bath. 257 parts of aqueous solution containing 148.5 parts of nickelous nitrate hexahydrate, $Ni(NO_3)_2.6H_2O$, and 8.6 parts of potassium nitrate, $KNO_3$, are poured over the chilled support. The resulting material is dried by heating overnight at 200° F. and then by heating for 2 hours at 300° F. The metal salts are decomposed by heating in air at 700° F. for 2 hours; and the catalyst is calcined in a muffle furnace at 700° F. for 2 hours. The so-prepared experimental catalyst contains 15.5% NiO (12.5% Ni), 1.8% $K_2O$, and 74.1% $Al_2O_3$. This catalyst had a nominal (or intended) composition of 15% NiO, 2% $K_2O$, and 83% $Al_2O_3$.

The calcined catalyst is reduced in hydrogen at 900° F. for 14-16 hours to give product containing 13.0% by weight of metallic nickel.

EXAMPLE VIII

The catalyst of this experimental example is prepared by the process of Example I except that the amounts of alumina, nickel nitrate, potassium nitrate, and chromium nitrate are such as to give a catalyst which (prior to reduction) contains 18.3% nickel oxide, 13.7% chromium oxide, 1.8% potassium oxide, and 66.1% aluminum oxide.

After calcination, this composition is reduced in hydrogen at 1200° F. for 16 hours to yield a product containing 11.0% by weight of metallic nickel.

EXAMPLE IX

A commercially-available nickel-potassium on Kieselguhr containing 35.3% nickel oxide and 0.44% sodium oxide on 7.1% silica, 46.3% alumina, and 10.8% calcium oxide is reduced in hydrogen at 1200° F. for 16 hours to yield product containing 22% metallic nickel.

EXAMPLE X

In this experimental example carried out in accordance with a preferred embodiment of this invention, the calcined alumina support is prepared as in Example I.

In the first portion of this example 340 parts of calcined alumina are soaked with an aliquot of a solution prepared by dissolving 395 parts of chromium nitrate nonahydrate and 21.5 parts of potassium nitrate in 1000 parts of water. After one hour, the remaining solution is decanted and the impregnated support is dried at 300° F., nitrate-decomposed at 700° F., and calcined for 2 hours at 1000° F. The procedure is repeated twice more until all the metal salt solution is absorbed by the initial charge of alumina. 383 parts of pre-catalyst are thus obtained.

In this second portion of this example, 293 parts of this pre-catalyst are cooled to 32° F. and impregnated with a solution of 250 parts of nickelous nitrate hexahydrate in 500 parts of water. The excess solution is decanted. The catalyst is dried at 300° F. and the cooled catalyst is reimpregnated with the remaining solution and dried again at 300° F. The catalyst is then nitrate-decomposed in air at 700° F. for 2 hours and calcined further in air at 700° F. for 2 hours. The product catalyst composition (362 parts of density 1.11) corresponds to the formula:

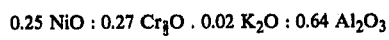
$$0.25\ NiO : 0.27\ Cr_3O . 0.02\ K_2O : 0.64\ Al_2O_3$$

and contains 17.7% NiO, 13.2% $Cr_2O_3$, 1.9% $K_2O$, and 61.6% $Al_2O_3$.

This catalyst is reduced in hydrogen at 900° F. for 14-16 hours to yield a product containing 13.0% by weight of metallic nickel.

In the following table there are set forth, for control examples I* to V* and for experimental examples VI to X, the following:

(a) the weight percent (dry basis) of NiO in the total catalyst;
(b) the weight percent of nickel corresponding to the amount of NiO — this being 78.5% of the percent of NiO;
(c) the weight percent (dry basis) of $Cr_2O_3$ in the total catalyst;
(d) the weight percent (dry basis) of potassium oxide, $K_2O$, in the total catalyst — in Example IX sodium oxide, $Na_2O$, is present rather than potassium oxide;
(e) the weight percent (dry basis) of support. In all examples the support is alumina except for Example III wherein the support is silica and Example IX wherein the support contains oxides of silicon, aluminum and calcium; and
(f) the weight percent of metallic nickel in the catalyst — as determined by the intensity of the (200) diffraction line.

TABLE

| Example | NiO | (Ni) | $Cr_2O_3$ | $K_2O$ | Support | Wt.% Metallic Ni |
|---|---|---|---|---|---|---|
| I* | 12.7 | 10.2 | 28.8 | 1.9 | 56.6 $Al_2O_3$ | 2.9 |
| II* | 13.2 | 10.7 | 32.9 | 1.9 | 51.9 $Al_2O_3$ | 3.4 |
| III* | 5.4 | 4.3 | — | 1.2 | 93.4 $SiO_2$ | 5.0 |
| IV* | 7.4 | 6.0 | 15.6 | 2.3 | 74.7 $Al_2O_3$ | 3.4 |
| V* | 12.6 | 10.2 | 2.6 | — | 84.7 $Al_2O_3$ | 2.7 |
| VI | 15.5 | 12.6 | 27.3 | 2.0 | 55.2 $Al_2O_3$ | 10.0 |
| VII | 17.0 | 13.9 | — | 2.0 | 81.1 $Al_2O_3$ | 13.0 |
| VIII | 18.3 | 15.0 | 13.7 | 1.8 | 66.1 $Al_2O_3$ | 11.0 |
| IX | 35.3 | 27.8 | — | 0.44 | 7.1 $SiO_2$ 46.3 $Al_2O_3$ 10.8 CaO | 22.0 |
| X | 18.7 | 15.4 | 14.0 | 2.0 | 65.2 $Al_2O_3$ | 13.0 |

The catalyst of each of these control and experimental examples was used in a steam demethylation reaction wherein reaction is carried out at 800° F. and 0 psig. Specifically, toluene and steam (at a mole ratio of 6 moles of steam per mole of toluene charge) are passed into contact with the catalyst in a standard manner. In each instance there is reported the toluene conversion (i.e., the weight percent of the charge toluene which is converted into other products).

The surface area (in square meters per gram of total catalyst) of nickel metal in each catalyst is calculated from determinations of (i) weight average crystal size determined from breadth of the (200) diffraction line, and (ii) the weight of metallic nickel.

The following table tabulates for each example the toluene conversion as a function of the surface area of nickel metal in the catalyst.

TABLE

| Example | Ni Metal Surface Area meters$^2$/gram | Toluene Conversion at 800° F Mole % Charge |
|---|---|---|
| I* | 1.3 | 2 |
| II* | 3.1 | 23 |
| III* | 4.1 | 12 |
| IV* | 4.4 | 1 |
| V* | 3.3 | 13 |
| VI | 8.8 | 84 |
| VII | 10.0 | 76 |
| VIII | 14.0 | 87 |
| IX | 18.0 | 82 |
| X | 24.0 | 87 |

From the results of the above typical illustrative examples, it is apparent that the plot of the data, determined by least squares analysis, indicates that toluene conversion increases as a function of increasing area of free nickel metal up to an asymptotic level of 75%-90% toluene conversion. The increase essentially terminates and the curve becomes substantially horizontal at a nickel metal area of ca 8 square meters per gram of total catalyst area.

The correlation between toluene conversion and metallic nickel surface area below 8 square meters per gram (when tested by determining the confidence in a non-zero slope of the least square line) is about 99.75%.

Results comparable to the above are observed when the charge hydrocarbon is:

| Example | Charge Hydrocarbon |
|---|---|
| XI | xylene(s) |
| XII | ethylbenzene |
| XIII | the reformate of the first table of the description supra |

Similarly, comparable results may be achieved when the catalyst contains:

| Example | Catalyst |
|---|---|
| XIV | Ni-alumina |
| XV | Pd-silica |
| XVI | Ni-Na-silica-alumina |
| XVII | Pt-alumina |
| XVII | Co-W-clay |
| XIX | Fe-Pt-K-zeolite |
| XX | Fe-Pd-Na-Mo-alumina |

Although this invention has been illustrated by reference to specific embodiments, it will be apparent to those skilled in the art that various changes and modifications may be made which clearly fall within the scope of this invention.

We claim:

1. A catalyst characterized by its ability to catalyze dealkylation of an alkylaromatic hydrocarbon at steam dealkylation conditions, which comprises:
   an alumina catalyst support bearing:
   an oxide of chromium;
   an oxide of nickel, said catalyst containing said nickel metal expressed as oxide, in amount of at least about 6 weight %, at least a portion of said nickel metal being in the form of free metal having a surface area of at least about 8 square meters per gram of total catalyst; and
   an oxide of potassium, said catalyst having been activated by the process which comprises:
   (a) maintaining the unactivated catalyst in a hydrogen atmosphere at 750° F.-1400° F. for 10-30 hours, thereby forming a hydrogen-treated catalyst;
   (b) maintaining the hydrogen-treated catalyst in a steam-hydrogen atmosphere at 750° F.-1400° F. for 2-10 hours, thereby forming a steamed hydrogen-treated catalyst; and (c) cooling the steamed hydrogen-treated catalyst to 650° F.–900° F. in a steam or steam-hydrogen atmosphere, thereby forming an activated catalyst.

2. A catalyst as claimed in claim 1 wherein said surface area is 8–24 square meters per gram of total catalyst.

3. A catalyst characterized by the ability to catalyze dealkylation of an alkylaromatic hydrocarbon at steam dealkylation conditions, having the formula:

$$a\ NiO : b\ Cr_1O : c\ K_2O : d\ Al_2O_3$$

wherein a is 0.002–0.75, b is 0.13–0.75, c is 0.003–0.75, and d is 0.15–0.93, at least a portion of said nickel metal being in the form of free metal having a surface area of at least about 8 square meters per gram of total catalyst, said catalyst having been activated by the process which comprises:

(a) maintaining the unactivated catalyst in a hydrogen atmosphere at 750° F.–1400° F. for 10–30 hours, thereby forming a hydrogen-treated catalyst;

(b) maintaining the hydrogen-treated catalyst in a steam-hydrogen atmosphere at 750° F.–1400° F. for 2–10 hours, thereby forming a steamed hydrogen-treated catalyst; and (c) cooling the steamed hydrogen-treated catalyst to 650° F.–900° F. in a steam or steam-hydrogen atmosphere, thereby forming an activated catalyst.

* * * * *